(12) United States Patent
Bell

(10) Patent No.: US 7,967,859 B2
(45) Date of Patent: Jun. 28, 2011

(54) PROSTHETIC EYE

(76) Inventor: Rupert C. Bell, Kalamazoo, MI (US)

( * ) Notice: Subject to any disclaimer, the term of this patent is extended or adjusted under 35 U.S.C. 154(b) by 183 days.

(21) Appl. No.: 11/901,332

(22) Filed: Sep. 17, 2007

(65) Prior Publication Data

US 2008/0119928 A1    May 22, 2008

Related U.S. Application Data

(60) Provisional application No. 60/860,174, filed on Nov. 20, 2006.

(51) Int. Cl.
*A61F 2/14* (2006.01)
(52) U.S. Cl. .......................... 623/6.64; 623/4.1
(58) Field of Classification Search .............. 623/5.11, 623/5.12, 5.13, 5.14, 6.64
See application file for complete search history.

(56) References Cited

U.S. PATENT DOCUMENTS

| | | | |
|---|---|---|---|
| 4,272,910 A | 6/1981 | Danz | |
| 5,026,392 A | 6/1991 | Gordon | |
| 5,061,279 A | 10/1991 | Friel | |
| 5,522,889 A * | 6/1996 | Baker et al. | 623/4.1 |
| 5,702,441 A * | 12/1997 | Zhou | 128/898 |
| 6,139,577 A | 10/2000 | Schleipman et al. | |
| 6,280,470 B1 * | 8/2001 | Peyman | 623/5.13 |
| 6,391,057 B1 | 5/2002 | Schleipman et al. | |
| 6,669,727 B1 | 12/2003 | Young | |
| 6,999,221 B1 | 2/2006 | Sarkisov et al. | |
| 2004/0049174 A1 * | 3/2004 | Peyman | 606/5 |

* cited by examiner

*Primary Examiner* — David H Willse
*Assistant Examiner* — Javier G Blanco
(74) *Attorney, Agent, or Firm* — Ian C. McLeod

(57) ABSTRACT

A prosthetic eye with an iris constructed of a photoresponsive, polymer based element. The photoresponsive element is responsive to light, so that the pupils constrict in the presence of light. The responsiveness of the pupils to light gives the prosthetic eye a more natural appearance.

15 Claims, 2 Drawing Sheets

PROSTHETIC EYE

CROSS-REFERENCE TO RELATED APPLICATION

This application claims benefit of U.S. Provisional Application No. 60/860,174 filed Nov. 20, 2006, which is incorporated herein by reference in its entirety.

STATEMENT REGARDING FEDERALLY SPONSORED RESEARCH OR DEVELOPMENT

Not Applicable.

REFERENCE TO A "COMPUTER LISTING APPENDIX SUBMITTED ON A COMPACT DISC"

Not Applicable.

BACKGROUND OF THE INVENTION (1) Field of the Invention

The present invention relates to a prosthetic eye with an iris constructed of a photoresponsive, polymer based element. The photoresponsive, polymer based element is responsive to light, so that the pupil constricts in the presence of light.

(2) Description of Related Art

U.S. Pat. No. 4,272,910 to Danz utilizes a photoelectric device such as a phototransistor for detecting environmental light conditions. In the front of the iris is an annular display of electro-optically sensitive material, i.e. a liquid-crystal display (LCD). In bright light, the LCD of the display appears transparent so that the iris is at a radius R1, while in reduced intensity light, the LCD appears dark so that the pupils appear enlarged.

U.S. Pat. No. 5,061,279 to Friel uses multiple layers of increasing diameter photochromic layers, while U.S. Pat. No. 6,669,727 to Young utilize polarized discs and eyeglasses to give the effect of a pupil responding to light. U.S. Pat. No. 5,026,392 to Gordon teaches a prosthetic eye with muscle connection points.

U.S. Pat. Nos. 6,139,577 and 6,391,057 to Schleipman et al. disclose a similar prosthetic eye. In the eye of Schleipman et al., a series of independently activated concentric rings of a visual display give a range from a fully dilated to a fully contracted pupil. Each of the above mentioned patents is incorporated herein by reference in their entirety. None of these references, however, teach a prosthetic eye having an iris comprising photoresponsive polymers. Therefore, there remains a need for an improved prosthetic eye.

SUMMARY OF THE INVENTION

The present invention relates to a prosthetic eye having a light responsive pupil comprising: a body of the prosthetic eye, the body having an internal cavity with an opening; an annular iris comprising a photoresponsive, polymer based element in the opening of the body, an inner radius of the iris defining the pupil; and a transparent cornea covering the opening in the body to enclose the iris, wherein when the iris is exposed to light the photoresponsive, polymer based element expands so as to constrict the pupil in response to the light. In further embodiments, the prosthetic eye further comprises oculomotor muscle anchors on an outer surface of the body of the prosthetic eye. In still further embodiments, the body is spheroid or disc shaped. In still further embodiments, the cornea is constructed of a transparent material. In further embodiments, the transparent material comprises polystyrene. In still further embodiments, a body of the prosthetic eye comprises a biocompatible material. In still further embodiments, the biocompatible material comprises polytetrafluoroethylene (PTFE). In further embodiments, the photoresponsive, polymer based element comprises latex rubber, photosensitive polyvinylidene fluoride (PVDF), or photosensitive flexible polyester film (e.g., photosensitive MYLAR).

Further still, the present invention relates to a prosthetic eye wherein the polymer based element comprises a polymeric material and an electrically expansive element operated by a battery to expand the iris in the presence of light and to contract the iris in absence of light. In further embodiments, the iris has expansive and contractive elements operated by the battery.

The present invention relates to a method for providing an artificial eye in an animal which comprises implanting the prosthetic eye into the socket of the animal. In further embodiments, the animal is a mammal. In further embodiments, the mammal is a human. In still further embodiments, the prosthetic eye is anchored on a surface of the socket.

OBJECTS

It is an object of the present invention to provide a prosthetic eye with a pupil that constricts in the presence of light.

These and other objects of the present invention will become increasingly apparent with reference to the following drawings and preferred embodiments.

DETAILED DESCRIPTION OF THE INVENTION

Figure 1:
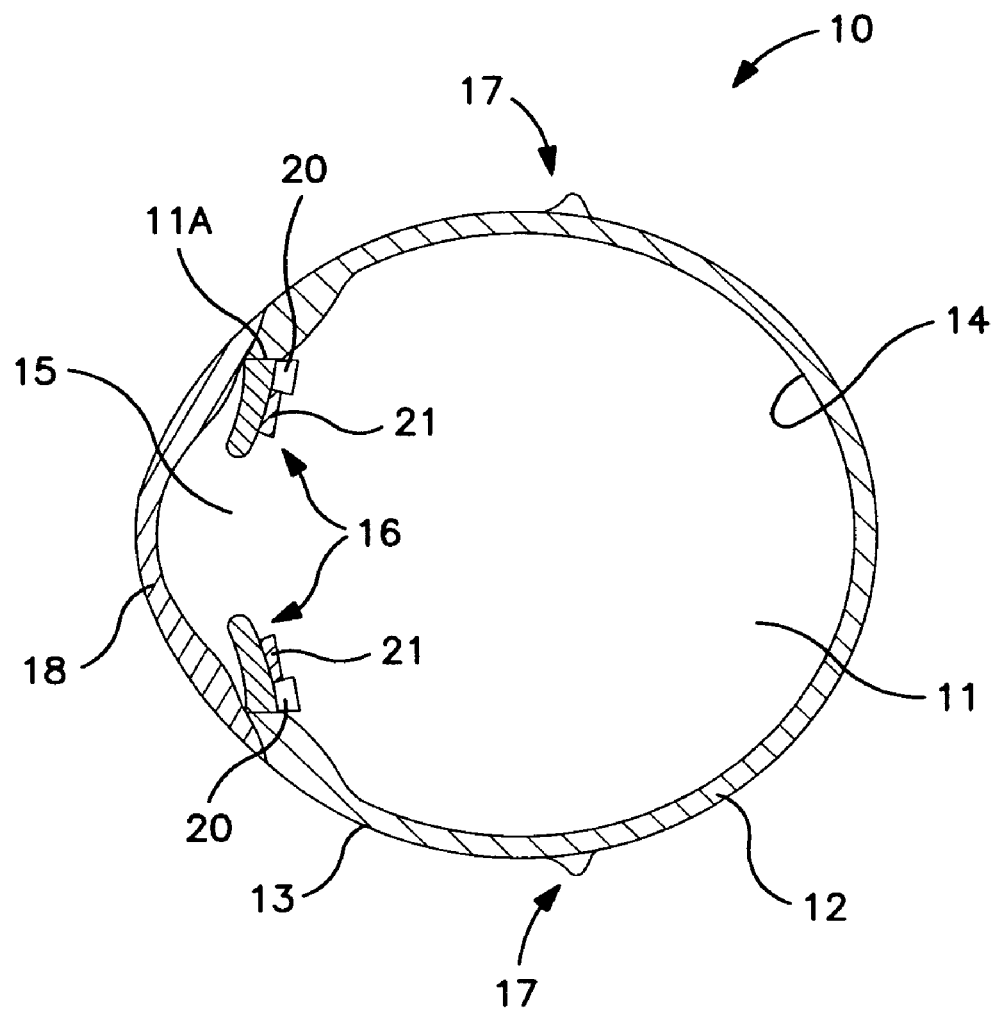
FIG. 1 illustrates a cross-section of one embodiment of a prosthetic eye 10 of the present invention that is spheroid shaped.

All patents, patent applications, government publications, government regulations, and literature references cited in this specification are hereby incorporated herein by reference in their entirety. In case of conflict, the present description, including definitions, will control.

The term "photoresponsive, polymer based element" as used herein refers to a polymeric material that mechanically deforms or is deformed, by means of one or more mechanisms or elements, when illuminated by light. In one embodiment, the material has a coefficient of thermal expansion (CTE) so that the material expands when heated. The material is heated when it absorbs energy from the light illuminating the material. Thus, the term "photoresponsive, polymer based element" includes, but is not limited to, polymeric materials such as latex rubber, photosensitive polyvinylidene fluoride (PVDF), and photosensitive mylar. The polymers are generally elastic enough to change shape. In other embodiments, mechanisms such as photostriction, electrostriction, and molecular reorientation play a role in the mechanical deformation of the material when it is illuminated by the light. U.S. Pat. No. 6,999,221 to Sarkisov et al., incorporated herein by reference in its entirety, describes photoresponsive materials.

The term "oculomotor" as used herein, relates to movement of the eyeball of a patient.

The term "biocompatible material" as used herein, refers to any material able to perform without eliciting any undesirable local or systemic effects in a host patient with a prosthestic eye constructed of the biocompatible material.

The present invention provides a prosthetic eye having a light responsive pupil comprising: (a) a body of the prosthetic eye, the body having an internal cavity with an opening; (b) an annular iris comprising a photoresponsive, polymer based element mounted in the opening of the body, an inner radius of the iris defining the pupil; and (c) a transparent cornea covering the opening in the body to enclose the iris, wherein when the iris is exposed to light the photoresponsive, polymer based element expands so as to constrict the pupil in response to the light. The present invention provides a more effective prosthesis for those who have lost an eye. The prosthetic eye has improved cosmetic value, as compared to conventional false eyes, in that it appears more natural. In addition, since some hallucinogenic drugs (LSD, psilocybin) and stimulants (cocaine) cause dilation of the pupils of drug users, persons with conventional false eyes have an increased risk of arrest due to having unresponsive pupils. The prosthetic eye of the present invention can minimize the chances of arrest of an innocent person with a prosthetic eye. In some embodiments, the present invention employs the negative coefficient of expansion of polymers to constrict the prosthetic pupil when the iris is exposed to light. In some embodiments, the iris will expand when heated by the light that illuminates it.

U.S. Pat. No. 6,999,221 to Sarkisov et al., incorporated herein by reference in its entirety, describes photoresponsive materials as a photosensitive portion of a flexible photomechanical body. Sarkisov et al. describes polymers of photosensitive polyvinylidene fluoride (PVDF) and photosensitive mylar as a photosensitive portion. The iris of the prosthetic eye of the present invention can incorporate the photoresponsive materials described by Sarkisov et al.

Figure 2:
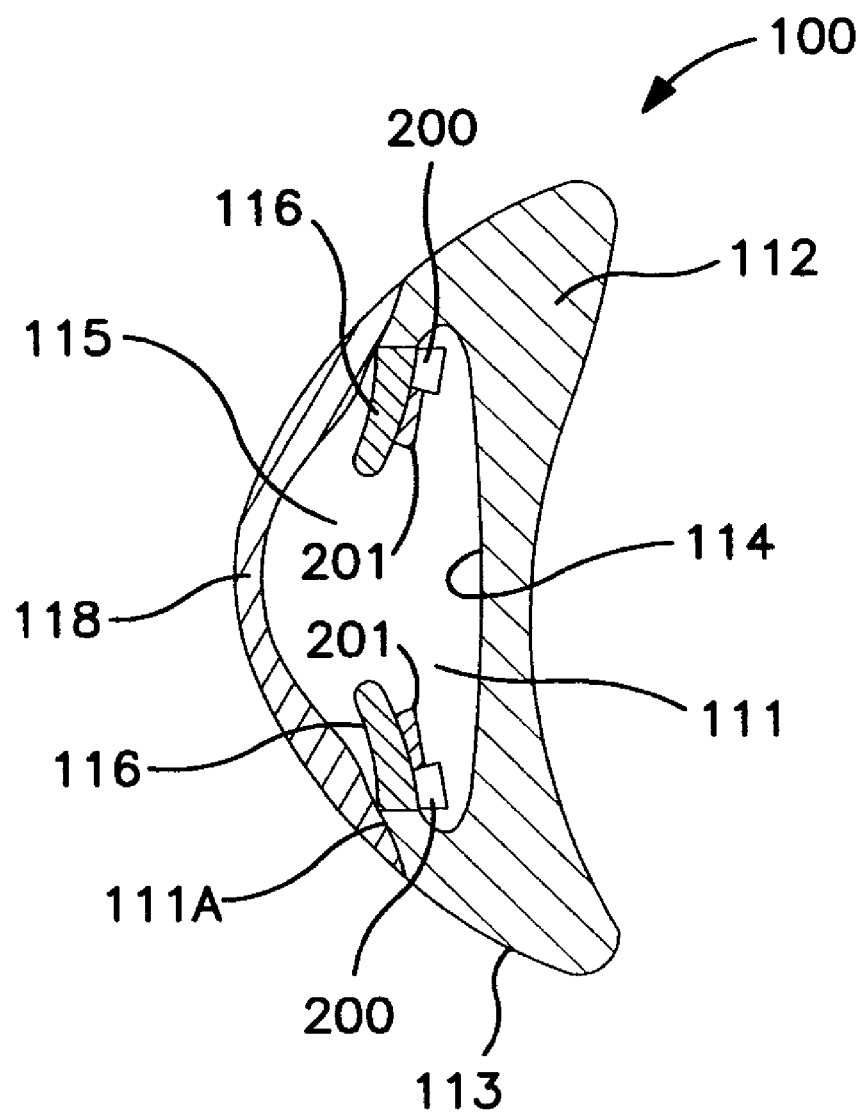
FIG. 2 illustrates a cross-section of a second embodiment of a prosthetic eye 100 that is disc shaped.

One embodiment of the prosthetic eye of the present invention is illustrated in FIG. 1. In the embodiment of FIG. 1, the prosthetic eye 10 is spheroid shaped; however, a disc shaped prosthetic eye 100 as illustrated in FIG. 2 are also encompassed by the present invention. As seen in FIGS. 1 and 2, the body 12, 112 of the prosthetic eye 10, 100 can be constructed of any biocompatible material such as, but not limited to, polytetrafluoroethylene (PTFE). In some embodiments, the biocompatible material of the body 12, 112 is white in color to resemble the sclera on the outer surface 13, 113. One example of a suitable polymer for the body 12, 112 is TEFLON® polytetrafluoroethylene (DuPont, Wilmington, Del.). The body 12, 112 of the prosthetic eye 10, 100 has an internal cavity 11, 111 with a circular opening 11A, 111A. The inner surface 14, 114 of the cavity 11, 111 in the body 12, 112 of the prosthetic eye 10, 100 is preferably black in color to give the pupil 15, 115 a black appearance. An annular shaped iris 16, 116 of the prosthetic eye 10, 100 is mounted in the opening 11A, 111A. The iris 16, 116 is constructed of a photoresponsive, polymer based element that is capable of expanding when illuminated with light. The iris 16, 116 of the prosthetic eye 10, 100 can be colored as appropriate. The iris 16, 116 has an inner radius that defines the pupil 15, 115. A transparent cornea 18, 118 covers the opening 11A, 111A in the body 12, 112 of the prosthetic eye 10, 100 so as to enclose the iris 16, 116. The cornea 18, 118 is constructed of a transparent material, such as, but not limited to polystyrene. In some embodiments, as illustrated in FIG. 1, the outer surface 13 of the prosthetic eye 10 has oculomotor muscle anchors 17 that allow for attachment of a patient's oculomotor muscles (not shown). An example of a prosthetic eye with tabs for connection of extra-ocular muscles to the prosthetic eye are described in U.S. Pat. No. 5,026,392 to Gordon, incorporated herein by reference in its entirety.

The cavity can be filled with a fluid to moisten the iris 16, 116 and to balance the weight of the artificial eye. Also, the iris 16, 116 can be a natural polymer. There can be nanoscale photosensor batteries 20, 200 to power photoresponsive changes in the polymeric iris. The batteries 20, 200 can be as shown in FIGS. 1 and 2. Elements in the iris 16, 116 can have electrically expansive and contractive elements 21, 201 which elongate or contract as a function of the presence or absence of light. These elements 20, 21 and/or 200, 201 can be in the body of the iris 16, 116. The elements 21 and the iris 16 can be wedge shaped in cross-section, tapering towards the pupil. This provides a more lifelike construction.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

I claim:

1. A prosthetic eye having a light responsive pupil comprising:
   (a) a body of the prosthetic eye, the body having an internal cavity with an opening;
   (b) an annular iris comprising a photoresponsive, polymer based element in the opening of the body, an inner radius of the iris defining the pupil; and
   (c) a transparent cornea covering the opening in the body to enclose the iris,
   wherein when the iris is exposed to light the photoresponsive, polymer based element expands so as to constrict the pupil in response to the light,
   wherein the body is spheroid or disc shaped, and
   wherein the photoresponsive, polymer based element mechanically deforms when illuminated by light such that the iris expands in the presence of light and contracts in the absence of light.

2. The prosthetic eye of claim 1, further comprising oculomotor muscle anchors on an outer surface of the body of the prosthetic eye.

3. The prosthetic eye of claim 1, wherein the cornea is constructed of a transparent material.

4. The prosthetic eye of claim 3, wherein the transparent material comprises polystyrene.

5. The prosthetic eye of claim 1, wherein a body of the prosthetic eye comprises a biocompatible material.

6. The prosthetic eye of claim 5, wherein the biocompatible material comprises polytetrafluoroethylene (PTFE).

7. The prosthetic eye of claim 1, wherein the photoresponsive, polymer based element comprises latex rubber, photosensitive polyvinylidene fluoride (PVDF), or photosensitive polyester.

8. The prosthetic eye of claim 1, wherein the photoresponsive, polymer based element comprises a polymeric material and an electrically expansive element operated by a battery to expand the iris in the presence of light and to contract the iris in absence of light.

9. The prosthetic eye of claim 8, wherein the iris has expansive and contractive elements operated by the battery.

10. A method for providing an artificial eye in an animal which comprises implanting the prosthetic eye of claim 1 into the socket of the animal.

11. The method of claim 10, wherein the animal is a mammal.

12. The method of claim 11, wherein the mammal is a human.

13. The method of claim 10, wherein the prosthetic eye is anchored on a surface of the socket.

14. The prosthetic eye of claim 1, wherein the photoresponsive, polymer based element comprises a polymeric material having a coefficient of thermal expansion that results in expansion of the polymeric material when heated.

15. A prosthetic eye having a light responsive pupil comprising:
   (a) a body of a prosthetic eye, the body having an internal cavity with an opening;
   (b) an annular iris comprising a photoresponsive, polymer based element in the opening of the body, an inner radius of the iris defining the pupil, wherein the photoresponsive, polymer based element mechanically deforms when the iris is illuminated by light and the photoresponsive, polymer based element expands so as to constrict the pupil in response to the light;
   (c) a transparent cornea covering the opening in the body to enclose the iris; and,
   (d) oculomotor muscle anchors on an outer surface of the body of the prosthetic eye,
   wherein the body is spheroid or disc shaped, and
   wherein the iris expands in the presence of light and contracts in the absence of light.

* * * * *